US011598674B2

(12) United States Patent
Gordon et al.

(10) Patent No.: US 11,598,674 B2
(45) Date of Patent: *Mar. 7, 2023

(54) SYSTEMS AND METHODS FOR LOGGING DATA IN HARSH ENVIRONMENTS

(71) Applicant: Maxim Integrated Products, Inc., San Jose, CA (US)

(72) Inventors: Jeffery Alan Gordon, Plano, TX (US); Scott Edward Jones, Highland Village, TX (US); Hal Kurkowski, Dallas, TX (US)

(73) Assignee: Maxim Integrated Products, Inc., San Jose, CA (US)

( * ) Notice: Subject to any disclaimer, the term of this patent is extended or adjusted under 35 U.S.C. 154(b) by 1315 days.

This patent is subject to a terminal disclaimer.

(21) Appl. No.: 15/778,121

(22) PCT Filed: Nov. 14, 2016

(86) PCT No.: PCT/US2016/061786
§ 371 (c)(1),
(2) Date: May 22, 2018

(87) PCT Pub. No.: WO2017/095611
PCT Pub. Date: Jun. 8, 2017

(65) Prior Publication Data
US 2020/0300710 A1    Sep. 24, 2020

Related U.S. Application Data

(60) Provisional application No. 62/261,749, filed on Dec. 1, 2015, provisional application No. 62/261,782, filed
(Continued)

(51) Int. Cl.
*G01K 13/02* (2021.01)
*G01K 1/022* (2021.01)
(Continued)

(52) U.S. Cl.
CPC ............... *G01K 1/022* (2013.01); *G01K 1/08* (2013.01); *G01K 7/42* (2013.01); *G01K 13/02* (2013.01);
(Continued)

(58) Field of Classification Search
CPC    G01K 1/022; G01K 1/08; G01K 7/42; G01K 13/02; G06F 11/3476; A61L 2/07;
(Continued)

(56) References Cited

U.S. PATENT DOCUMENTS 6,212,937 B1 * 4/2001 Hubert ................ G01K 1/02
73/23.31
6,406,181 B1 * 6/2002 Mueller ............ G01N 27/4071
374/185

(Continued)

FOREIGN PATENT DOCUMENTS

CA        2847886 A1 * 3/2013 ............ G01N 27/40
CN      110196120 A  * 9/2019 ............... G01K 1/14
(Continued)

OTHER PUBLICATIONS

International Search Report dated Jan. 31, 2017, in International PCT Patent Application No. PCT/US2016/061786, filed Nov. 14, 2016 (2pgs).
(Continued)

*Primary Examiner* — Gail Kaplan Verbitsky
(74) *Attorney, Agent, or Firm* — North Weber & Baugh LLP; Michael North

(57) ABSTRACT

Systems and methods of the present invention allow to determine ambient gas temperature in harsh environments such as in a steam autoclave chamber during a sterilization process. In certain embodiments of the invention, temperature data is gathered using a sensor that is placed in an enclosed electronics-based temperature logging device. A
(Continued)

capsule seals the temperature logging device except for a through hole that, during regular operation, allows gas to directly contact a surface of the temperature logging device in order to reduce a time lag between the data logging device and an ambient gas. As a result, the data logging device accurately can track temperature variations when placed, for example, inside a chamber.

14 Claims, 4 Drawing Sheets

Related U.S. Application Data on Dec. 1, 2015, provisional application No. 62/261,783, filed on Dec. 1, 2015.

(51) Int. Cl.
*G01K 7/42* (2006.01)
*G01K 1/08* (2021.01)
*G06F 11/34* (2006.01)
*G01K 7/01* (2006.01)
*A61L 2/28* (2006.01)

(52) U.S. Cl.
CPC ............ *G06F 11/3476* (2013.01); *A61L 2/28* (2013.01); *G01K 7/015* (2013.01)

(58) Field of Classification Search
CPC .... A61L 2202/14; G01M 99/008; B08B 3/00; B08B 5/00; B08B 2230/01
See application file for complete search history.

(56) References Cited

U.S. PATENT DOCUMENTS

| | | | | |
|---|---|---|---|---|
| 7,726,876 B2* | 6/2010 | Laverdiere | ................ | G01J 5/02 |
| | | | | 374/208 |
| 8,528,430 B2* | 9/2013 | Jilderos | ................... | F16L 37/42 |
| | | | | 73/866.5 |
| 8,852,513 B1* | 10/2014 | Speer | ................ | G01N 33/0014 |
| | | | | 422/83 |
| 9,310,277 B2* | 4/2016 | Peng | ....................... | G01M 17/02 |
| 9,606,010 B2* | 3/2017 | Kaiser | ................ | G01L 19/0092 |
| 9,841,335 B2* | 12/2017 | Rueth | ........................ | G01L 9/00 |
| 10,668,177 B1* | 6/2020 | D'Onofrio | ................ | A61L 2/07 |
| 10,989,610 B2* | 4/2021 | Xiao | ........................ | G01K 1/08 |
| 2003/0219052 A1 | 11/2003 | Edigio | | |
| 2006/0169294 A1* | 8/2006 | Kaier | ..................... | A61B 5/073 |
| | | | | 128/903 |
| 2006/0225486 A1 | 10/2006 | Kellerman et al. | | |
| 2006/0249402 A1* | 11/2006 | Snow | ..................... | B82Y 30/00 |
| | | | | 205/777 |
| 2008/0250862 A1* | 10/2008 | Nakabayashi | ...... | G01L 19/0092 |
| | | | | 73/114.37 |
| 2008/0272131 A1* | 11/2008 | Roberts | .................. | G01K 1/024 |
| | | | | 374/E1.004 |
| 2011/0128129 A1 | 6/2011 | Graczyk et al. | | |
| 2012/0266451 A1* | 10/2012 | Boguhn | .................. | G01F 1/684 |
| | | | | 29/592.1 |
| 2014/0070078 A1 | 3/2014 | Land et al. | | |
| 2015/0330840 A1* | 11/2015 | Lukach, Jr. | .............. | G01K 1/10 |
| | | | | 374/208 |

FOREIGN PATENT DOCUMENTS

| | | | | | |
|---|---|---|---|---|---|
| CN | 210981571 | U | * | 7/2020 | |
| CN | 111707726 | A | * | 9/2020 | ......... G01N 27/4163 |
| DE | 3924949 | A | * | 1/1991 | ............. G01K 17/08 |
| DE | 112011105807 | T5 | * | 7/2014 | ............... G01D 9/00 |
| GB | 2521462 | A | * | 6/2015 | ............. G01K 13/02 |
| JP | H024531 | U | | 1/1990 | |
| JP | 2001505998 | A | | 5/2001 | |
| JP | 2449232 | Y | * | 9/2001 | |
| JP | 2004097330 | A | * | 4/2004 | ............ C12M 37/02 |
| JP | 2012110810 | A | * | 6/2012 | |
| JP | 2013543136 | A | * | 11/2013 | |
| JP | 201587146 | | * | 5/2015 | |
| KR | 20150031734 | A | * | 3/2015 | |
| WO | WO-2006048192 | A1 | * | 5/2006 | .............. F01N 11/00 |
| WO | WO-2007120619 | A2 | * | 10/2007 | ............ C12M 31/10 |
| WO | WO-2019083814 | A1 | * | 5/2019 | .............. F28G 1/16 |
| WO | WO-2020097154 | A1 | * | 5/2020 | ............. C09D 11/50 |

OTHER PUBLICATIONS

Written Opinion dated Jan. 31, 2017, in International PCT Patent Application No. PCT/US2016/061786, filed Nov. 14, 2016 (5pgs).

\* cited by examiner

SYSTEMS AND METHODS FOR LOGGING DATA IN HARSH ENVIRONMENTS

CROSS REFERENCE TO RELATED PATENT APPLICATIONS

The present application is a U.S. 371 National Stage of PCT Patent Application No. PCT/US16/61786, entitled "SYSTEMS AND METHODS FOR LOGGING DATA IN HARSH ENVIRONMENTS," naming as inventors Jeffery Alan Gordon, Scott Edward Jones and Hal Kurkowski, and filed Nov. 14, 2016, which claims priority benefit, under 35 U.S.C. § 119(e), U.S. Provisional Patent Application No. 62/261,749, entitled "APPARATUS FOR LOGGING DATA IN HARSH ENVIRONMENTS," naming as inventors Jeffery Alan Gordon, Scott Edward Jones, and Hal Kurkowski, U.S. Provisional Patent Application No. 62/261,782, entitled, "INDICATOR OF STERILIZATION EFFICACY USING A DATA LOGGER WITH CLOUD/SOFTWARE APPLICATION," naming as inventors Michael James D'Onofrio, Carlos Manuel Contreras, and Raghunath Puttaiah, and U.S. Provisional Patent Application No. 62/261, 783, entitled "ALGORITHM TO CORRECT LAG BETWEEN INTERNAL TEMPERATURE SENSOR AND AMBIENT GAS," naming as inventors Victor Levi, Michael James D'Onofrio, and Raghunath Puttaiah, which applications were filed Dec. 1, 2015, and which applications are hereby incorporated herein by reference in their entireties.

BACKGROUND

A. Technical Field

The present invention relates to apparatus for data acquisition, and more particularly, to apparatus for logging temperature data in harsh environments.

B. Background of the Invention

Over the years, various devices for acquiring and storing temperature data have been developed to trace the history of ambient temperature surrounding the devices. Manufacturers and/or distributors send the device along with their products, such as drugs, that are sensitive to temperature changes, where the products need to remain within a preset temperature range to keep their original efficacy. The receivers of the products retrieve the temperature data stored in the device and check if the temperature of the products was outside the preset range during transportation.

A conventional device for logging temperature data includes various electronic components enclosed in a housing (or, equivalently, packaging or capsule). Typically, the capsule is not hermetic and cannot protect the electronic components under harsh environments, such as autoclave for steam sterilization at high pressure and high temperature. Some of the conventional devices are designed to operate at high temperature environments, but cannot prevent the ingress of moisture into the capsule that damages the electronic components. As such, the conventional devices can survive only a few sterilization cycles at best and thus are not suitable for logging data during multiple cycles.

Some conventional devices for logging temperature data have been designed to operate at relatively large time constants. For instance, a typical device for monitoring the ocean temperature may have a water-proof capsule and take a sample at every hour. Typically, the capsule is made of thick metal plate, and there is a time lag between the ocean water and the temperature inside the capsule. In such a case, the time constant for the device is in the order of minute, and thus, the time lag due to the large thermal mass of the capsule may not affect the accuracy of the data.

In other applications, such as autoclave for steam sterilization, the time constant is relatively short since the temperature inside the autoclave rises from room temperature to 100° C. quite quickly. When a conventional device for logging temperature data is placed inside the autoclave, the device may not be able to keep up with the temperature change due to the thermal resistance of the capsule material. The thermal resistance may result in false reading of the ambient gas temperature.

In a conventional sterilization autoclave, a chemical indicator (integrator or emulator) is used to measure the temperature inside the autoclave. The chemical indicator (CI) has a temperature sensitive strip that changes its color depending on the temperature and stays changed permanently. However, the conventional chemical indicator cannot be used to trace the temperature as a function of time during the sterilization cycle.

In another conventional sterilization autoclave, a biological indicator (BI) is used to determine whether the sterilization cycle is successful (i.e., decide pass/fail of the cycle). The biological indicator is a paper strip filled with a preset number of *Geobacillus stearothermophilus* spores. Typically, a sterilization cycle is designed to achieve a 12 log reduction in spores half way through a cycle. However, in reality, they are all killed before a half cycle due to the stress of the temperature ramp up conditions. Thus, the biological indicator may indicate the sterilization condition of an early portion of the cycle rather than the whole cycle. In addition, the biological indicator has a long turnaround time since the spore sample may need to be sent to a lab and, depending on the type of spores, incubation may be needed. Furthermore, the conventional CI and BI techniques require manual recording of paper logbooks, which is less efficient and more costly than electronic recording and processing of the logged data.

As such, there is a need for a device for electronically logging temperature data in harsh environments, where the capsule of the device can protect the electronic components of the device from ingress of moisture and the time constant of the capsule is short enough to accurately measure the ambient gas temperature around the device.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

In the following description, for the purposes of explanation, specific details are set forth in order to provide an understanding of the invention. It will be apparent, however, to one skilled in the art that the invention can be practiced without these details. One skilled in the art will recognize that embodiments of the present invention, described below, may be performed in a variety of ways and using a variety of means. Those skilled in the art will also recognize additional modifications, applications, and embodiments are within the scope thereof, as are additional fields in which the invention may provide utility. Accordingly, the embodiments described below are illustrative of specific embodiments of the invention and are meant to avoid obscuring the invention.

A reference in the specification to "one embodiment" or "an embodiment" means that a particular feature, structure, characteristic, or function described in connection with the embodiment is included in at least one embodiment of the invention. The appearance of the phrase "in one embodiment," "in an embodiment," or the like in various places in the specification are not necessarily all referring to the same embodiment.

Furthermore, connections illustrated in the figures between components may be modified or otherwise changed through the addition thereto of intermediary components, without departing from the teachings of the present invention.

Figure 1A:
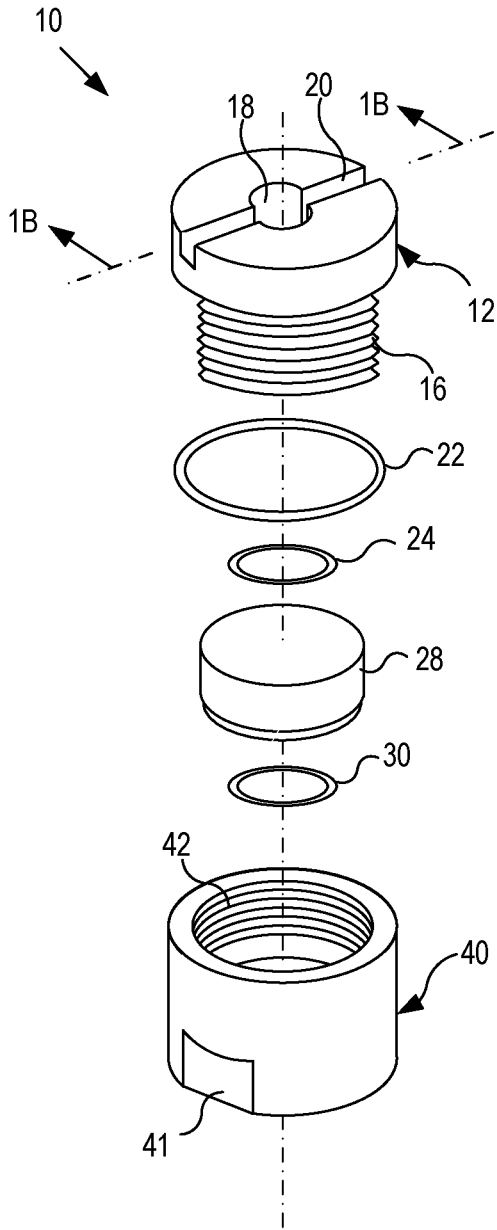
FIGS. 1A-1C show a package for logging temperature data according to one embodiment of the present invention.
Figure 1B:
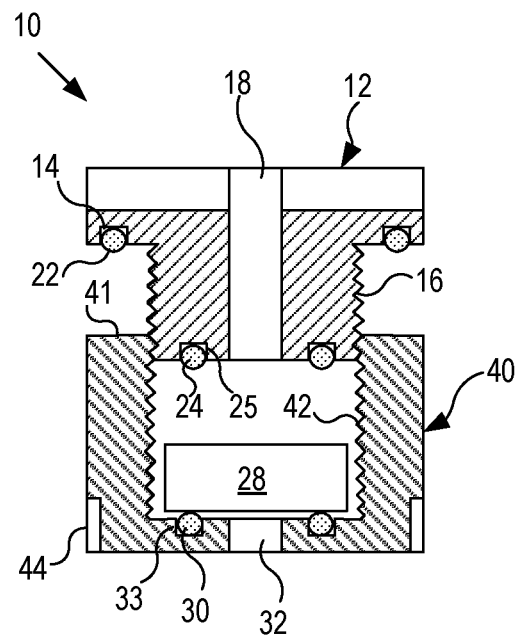
Figure 1C:
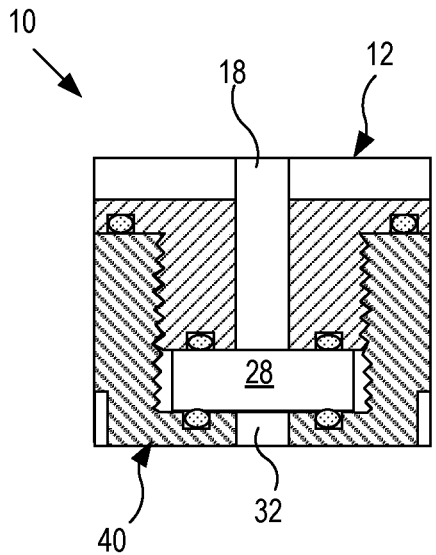

FIG. 1A shows an exploded view of a package 10 for logging temperature data according to one embodiment of the present invention. As depicted in FIG. 1A, the package 10 includes: a capsule having a plug 12, a base 40 and O-rings 22, 24, and 30; and a temperature data logger (or, shortly, data logger) 28 for logging temperature data under harsh environments. In embodiments, the data logger 28 may be an integrated circuit (IC)-based temperature data logger. FIG. 1B shows a cross sectional view of the package 10, taken along the direction 1B-1B, where the male thread 16 of the plug 12 is slightly engaged into the female thread 42 of the base 40. FIG. 1C shows the package 10, where the plug 12 is fully engaged into the base 40.

For the purpose of illustration, the package 10 is described as a temperature data logging device for a steam autoclave chamber, i.e., the package 10 is mounted inside a steam autoclave chamber and logs temperature data during sterilization cycles of the autoclave. For instance, an exemplary operational condition of the steam autoclave has the temperature of 140° C. and the pressure of 2 atmosphere, and each cycle may last 35-40 minutes, and the package 10 is designed to survive more than hundred cycles without being damaged by the ambient gas. However, it should be apparent to those of ordinary skill in the art that the package 10 may be applied to other test environments. Also, it should be apparent to those of ordinary skill in the art that the package 10 may be calibrated to accommodate different operational temperature range.

The plug 12 includes: a slot 20 for receiving a tool, such as torque wrench, for turning the plug 12 relative to the base 40; and a through hole 18 that allows the ambient gas to directly contact the top surface of the data logger 28 during operation. Since the ambient gas including hot steam is in direct contact with the data logger 28, the thermal lag between the chamber environment and the data logger 28 is reduced so that the data logger 28 can accurately track the temperature variation inside the chamber.

The O-rings 22, 24, and 30 are used to prevent ingress of moisture into the data logger 28. The O-ring 22 rests on a groove 14 that is formed on the plug 12. The O-ring 22 is compressed by the lip 41 of the base 40 when the plug 12 is fully engaged into the base 40, as shown in FIG. 1C, to thereby preventing ingress of the ambient gas through the gap between the male thread 16 and the female thread 42.

The O-rings 24 and 30 rest on grooves 25 and 33, respectively. When the package 10 is assembled, the O-rings 24 and 30 are compressed by the top and bottom surfaces of the data logger 28, respectively, to thereby prevent ingress of the ambient gas through the gaps between the capsule and the data logger 28.

The base 40 includes a through hole 32 that allows the ambient gas to directly contact the bottom surface of the data logger 28 during operation. Since the ambient gas is in direct contact with the data logger 28, the thermal lag between the chamber environment and the data logger 28 is reduced so that the data logger 28 can accurately track the temperature variation inside the chamber. The base 40 also includes a notch/recess 44 so that a proper device securely holds the base in place during assembly of the package 10.

If the package 10 is assembled while the O-rings 22, 24, and 30 are dry, the O-rings may not properly seal the space surrounding the data logger 28 due to pinching, crimping, or twisting of the O-rings. To avoid such deformation of the O-rings, small amount of grease is applied to the O-rings. The grease also holds the O-rings in their corresponding grooves temporarily during assembly. For instance, the O-rings 22 and 24 remain seated on the grooves 14 and 25, respectively, by the grease when the plug 12 is flipped over during assembly, as shown in FIG. 1B.

It is noted that the package 10 may be mounted in the autoclave chamber with other items, such as medical instruments, being sterilized. If the package 10 releases any toxic material into the autoclave chamber, the items may be contaminated by the toxic material. As such, all of the components, including the grease, of the package 10 are tested to ensure that none of the components release toxins during sterilization cycles.

The capsule is reusable, i.e., the user can disengage the male thread 16 from the female thread 42, replace the data logger 28, and reassemble the package 10. During this process, the user may not place one or more of the O-rings 22, 24 and 30 properly i.e., the user may misalign the O-rings on resealing. In embodiments, to obviate the improper reassembly by the user, a small amount of glue may be applied to the threads so that the plug and base are glued together.

Figure 2:
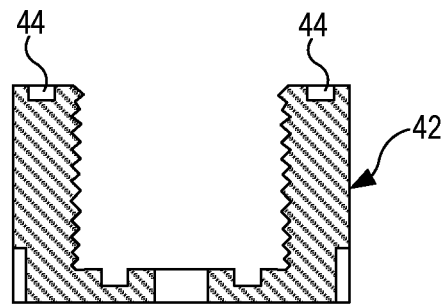
FIG. 2 shows a cross sectional view of a base according to one embodiment of the present invention.

FIG. 2 shows a cross sectional view of a base 42 of a capsule according to one embodiment of the present invention. As depicted, the base 42 is similar to the base 40 in FIGS. 1A-1C, with the difference that the base 42 includes an O-ring groove 44 that the O-ring 22 rests on. It should be apparent to those of ordinary skill in the art that the package 10 may include other suitable types of sealing mechanisms to prevent the ingress of the ambient gas into the data logger 28.

The material for the plug 12 and base 40 (or 42) may be chosen for its mechanical properties (i.e., they remain stable during both long and short-term exposure to high temperature and pressure), inherent flame resistance, and outstanding chemical resistance (i.e., inert to high temperature steam, strong bases, fuels and acids). In embodiments, the plug and base are formed of a polymer, such as polyphenylene sulfide (PPS) Likewise, the material for the O-rings 22, 24, and 30 may be chosen for their mechanical strength and chemical qualities. In embodiments, the O-rings are formed of silicon, where the silicon O-rings are also resistant to sunlight, ozone, oxygen, and UV light.

Figure 3:
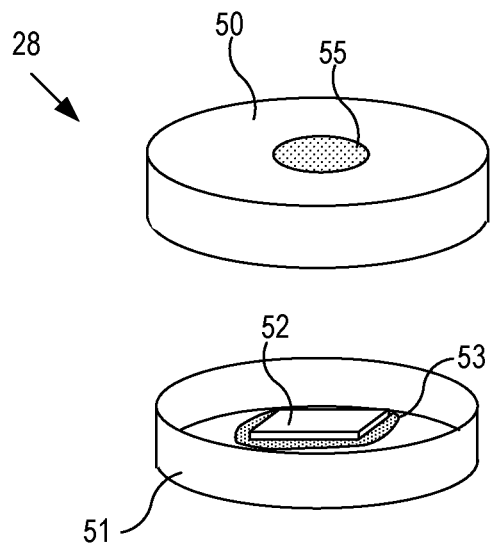
FIG. 3 shows an integrated circuit (IC)-based temperature data logger according to one embodiment of the present invention.

FIG. 3 shows an integrated circuit (IC)-based temperature data logger 28 according to one embodiment of the present invention. As depicted, the data logger 28 includes: a top cover 50; a bottom cover 51; an electrical circuitry 52 for measuring and storing the temperature data; and a securing element 53 that secures the electrical circuitry 52 to the bottom cover 51. When the data logger 28 is assembled, the top and bottom covers 50 and 51 form a housing and the electrical circuitry 52 is disposed in the inner space of the housing. In embodiments, the top and bottom covers 50 and 51 may provide water-proof sealing against fluid.

In embodiments, the top and bottom covers 50 and 51 may be formed of electrically conducting material and operate as two electrodes that are electrically connected to the electrical circuitry 52. For instance, a suitable electrical device may communicate the data logged in the data logger 28 through the top and bottom covers 50 and 51. The top and bottom covers 50 and 51 are formed of material having high thermal conductivity, such as metal, so that the lag between the temperature of the autoclave chamber and the temperature inside the covers 50 and 51 is minimized. The securing element 53 is formed of material having a high thermal conductivity, such as heat conducting glue, to minimize the thermal lag between the temperature inside the covers 50 and 51 and the temperature inside the electrical circuitry 52.

Unlike the conventional temperature loggers, a portion 155 of the top cover 50 is directly exposed to the ambient gas via the through hole 18 without damaging the electric circuitry 52 during operation. Likewise, a portion of the bottom cover 51 is directly exposed to the ambient gas via the through hole 32 during operation. This feature allows the data logger 28 to have minimal temperature lag, i.e., the data logger 28 can track the ambient gas temperature more accurately.

Figure 4:
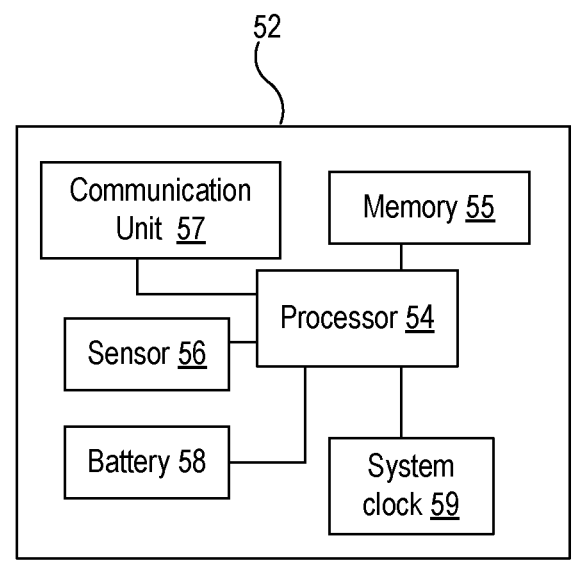
FIG. 4 shows a schematic diagram of an electric circuitry of the electronics-based temperature data logger in FIG. 3 according to one embodiment of the present invention.

FIG. 4 shows a schematic diagram of the electronic circuitry 52 of the electronics-based temperature data logger 28 in FIG. 3 according to one embodiment of the present invention. In embodiments, the electrical circuitry 52 may be an application-specific integrated circuit (ASIC) and include: a processor 54 for operating various components of the circuitry 52; a sensor 56 for measuring temperature; a battery 58 for providing electrical power to the circuitry 52; a communication unit 57 for communicating data to an external device; a memory 55 for storing the measured temperature data; and a system clock 59 for generating clock signals for the circuitry 52. It is noted that, depending on the application, the circuitry 52 may include additional components, such as additional sensors, and one or more of the components of the circuitry 52 may be omitted.

In embodiments, the processor 54 may be programmed to measure the temperature inside the data logger 28 at a preset time and/or repeat measurements at a preset time interval. In embodiments, the processor 54 may receive the clock signals from the system clock 59 and cause the sensor 56, such as digital temperature sensor, to measure the temperature as scheduled. Then, the processor 54 may store the data into the memory 55, where the memory 55 may be a static RAM, for instance. In embodiments, to minimize the power consumption, the processor 54 may wake up at the scheduled time to measure the temperature and goes back to sleep mode after measurement is completed.

Figure 5:
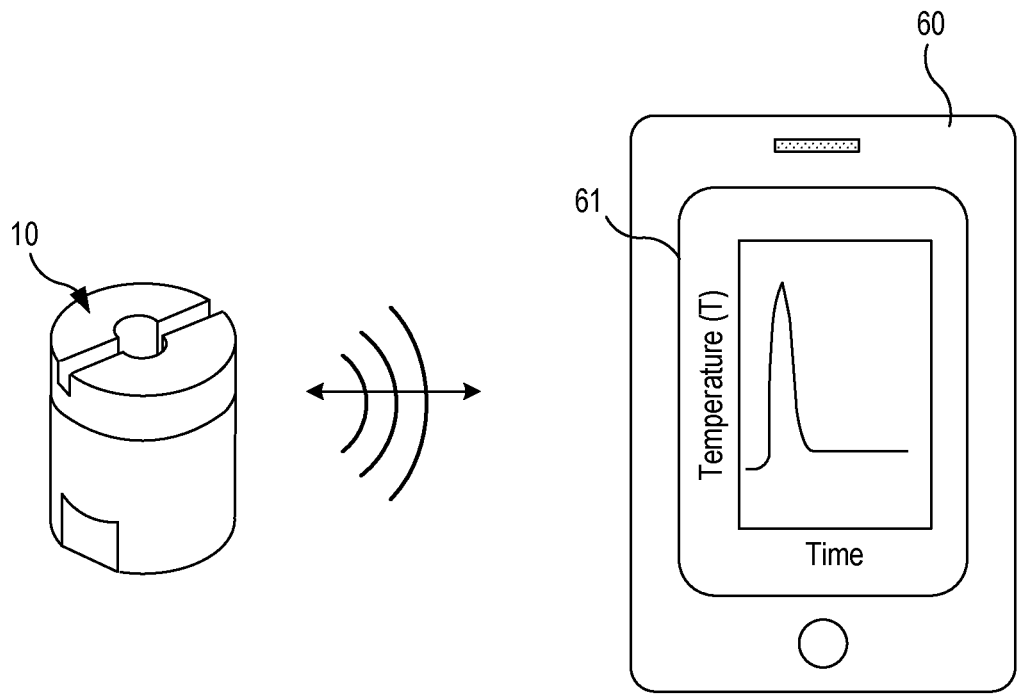
FIG. 5 shows a data communication between the package in FIG. 1A and a mobile device according to one embodiment of the present invention.

In embodiments, the processor 54 may communicate the stored data to an external device through the communication device 57 and/or the processor 54 may be controlled/programmed through the communication device 57. In embodiments, the communication unit 57 may be a wireless communication device. FIG. 5 shows a data communication between the package 10 and a mobile device 60 according to one embodiment of the present invention.

In embodiments, the user may install an application on the mobile device 60 so that the user can set up the parameters on the circuitry 52, such as time and frequency of data sampling, before the package 10 is mounted in the autoclave. After a sterilization cycle(s), the user may retrieve the stored data from the package 10 using the mobile device 60 and a suitable application may display the temperature data on the display 61 of the mobile device 60. It is noted that the user may control and communicate to the package 10 using other suitable external devices. For instance, in embodiments, the user may use a computer/server in place of the mobile device 60.

Figure 6:
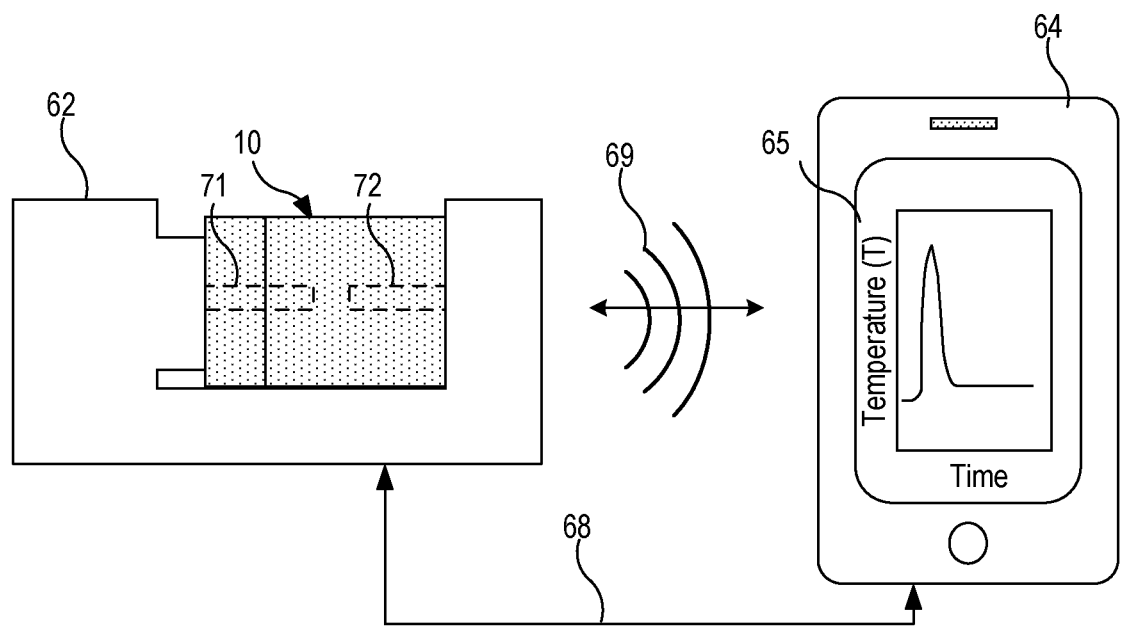
FIG. 6 shows a data communication between the package in FIG. 1A and a mobile device according to one embodiment of the present invention.

FIG. 6 shows a data communication between the package 10 and a mobile device 64 according to one embodiment of the present invention. As depicted, the package 10 may be docked in a reader 62 that can retrieve data stored in the package 10 and send the retrieved data to the mobile device 64. In embodiments, the reader 62 may have two spring-loaded electrodes 71 and 72 that make electrical contact to the top and bottom surfaces of the data logger 28, respectively, and extract the data stored in the package 10. Also, in embodiments, the reader 62 may be used to transmit electrical signals from the mobile device 64 to the package 10 so that the user can program the electrical circuitry 52.

After a sterilization cycle(s), the user may retrieve the stored data from the package 10 using the mobile device 64 and a suitable application installed in the mobile device 64 displays the temperature data on the display 65 of the mobile device 64. It is noted that the user may control and communicate to the package 10 using other suitable external device. For instance, in embodiments, the user may use a computer/server in place of the mobile device 64. In some embodiments, the reader 62 may exchange electrical signals with the mobile device 64 through wireless communication 69, as shown in FIG. 6, or through wire 68, such as universal serial bus (USB) connection.

Figure 7A:
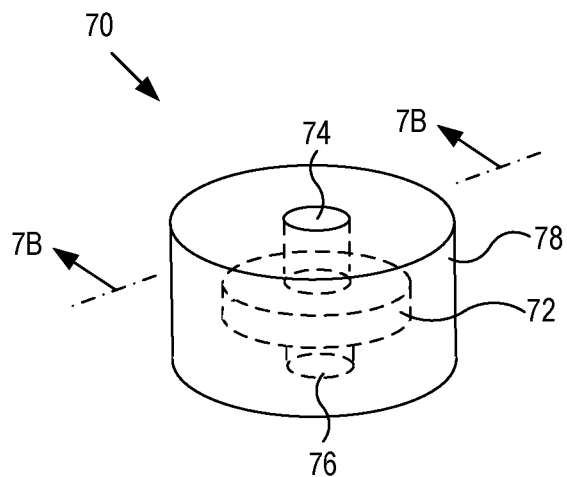
FIGS. 7A-7B show a package for logging temperature data according to one embodiment of the present invention.
Figure 7B:
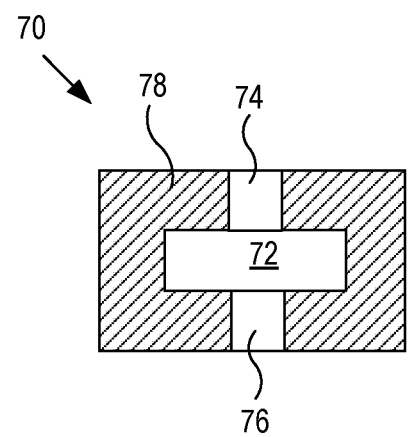

FIG. 7A shows a perspective view of a package 70 for logging temperature data according to one embodiment of the present invention. FIG. 7B shows a cross sectional view of the package 70, taken along the direction 7B-7B. As depicted, the package 70 includes: a temperature data logger 72 that has the similar structure and functions as the data logger 28 in FIGS. 3 and 4; and a capsule 78 surrounding the temperature logger 72. In embodiments, the capsule 78 is formed of the same material as the plug 12. In embodiments, the entire portion of the capsule 78 may be formed by a molding process.

The capsule 78 has two holes 74 and 76 that extend to the top and bottom surfaces of the data logger 72, respectively. The two holes 74 and 76 allow the ambient gas to directly contact the data logger 72, minimizing the lag between the temperature of the ambient gas and the temperature inside the data logger 72.

In embodiments, the data logger 28 (or 70) is wrapped in a pouch before the data logger is mounted in the autoclave. In other embodiments, the data logger 28 (or 70) is not wrapped in a pouch/cassette if the temperature lag introduced by the pouch affects the accuracy of the temperature measurement.

In embodiments, the package 10 (or 70) is mounted in a steam sterilization chamber to track the temperature profile of the ambient gas and create an electronic time/temperature record. Based on the analysis of the temperature data, it can be determined whether the sterilization cycle is adequate to sterilize the tools inside the autoclave. The electronic record generated by the package 10 (or 70) is more precise and lends itself to storage, transmittal, and automatic/electronic handling more rapidly than the conventional chemical or biological approaches.

What is claimed is:

1. A system for measuring gas temperature, the system comprising:
    an electronic temperature data logger that comprises:
        an enclosure comprising a top cover and a bottom cover, at least one of the top and bottom cover comprising a surface that in regular operation is exposed to an ambient gas; and
        a sensing element that generates temperature data from a measured gas temperature, the sensing element being located within the enclosure and being disposed on a circuit that comprises one or more processors;
    a capsule that at least partially seals the enclosure and comprises at least one through hole that provides access to the surface; and
    a system clock coupled to the one or more processors, the system clock generates clock signals to control a timing of the circuit.

2. The system according to claim 1, wherein the at least one through hole reduces a thermal lag between the measured gas temperature and an gas temperature.

3. The system according to claim 1, wherein the enclosure is removably attached to the capsule.

4. The system according to claim 1, wherein the at least one of the top cover or bottom cover is electrically connected to the circuit, the at least one of the top cover or bottom cover serving as an electrode.

5. The system according to claim 1, wherein the one or more processors comprise a power saving circuit comprising a sleep mode that is activated between two measurement cycles.

6. The system according to claim 1, further comprising a communication circuit coupled to the one or more processors, the communication circuit being coupled to a wireless communication device that communicates the temperature data to a reader.

7. The system according to claim 1, wherein the sensing element is a digital temperature sensor.

8. The system according to claim 1, wherein the circuit is affixed to the enclosure via a thermal conductor.

9. The system according to claim 1, wherein the least one of the top and bottom cover are formed of material having high thermal conductivity.

10. A method for measuring a gas temperature, the method comprising:
    placing an enclosure into a capsule, the enclosure comprising a sensing element disposed on an integrated circuit, the capsule at least partially seals the enclosure and comprises at least one through hole that provides access to a surface of the enclosure;
    placing the capsule into a chamber; and
    using the sensing element to gather temperature data within the chamber to determine a gas temperature, wherein the sensing element is coupled to a power saving circuit that activates a sleep cycle between two measurement cycles.

11. A method for measuring a gas temperature, the method comprising:
    placing an enclosure into a capsule, the enclosure comprising a sensing element disposed on an integrated circuit, the capsule at least partially seals the enclosure and comprises at least one through hole that provides access to a surface of the enclosure;
    placing the capsule into a chamber; and
    using the sensing element to gather temperature data within the chamber to determine a gas temperature, wherein the enclosure comprises a cover that is electrically connected to the integrated circuit and serves as an electrode.

12. A method for measuring a gas temperature, the method comprising:
    placing an enclosure into a capsule, the enclosure comprising a sensing element disposed on an integrated circuit, the capsule at least partially seals the enclosure and comprises at least one through hole that provides access to a surface of the enclosure;
    placing the capsule into a chamber; and
    using the sensing element to gather temperature data within the chamber to determine a gas temperature, wherein wherein the gas temperature is logged during a plurality of sterilization cycles.

13. An apparatus comprising:
    an enclosure comprising a top cover and a bottom cover, at least one of the top cover or bottom cover comprising a surface that, in regular operation, is exposed to a gas; and
    a sensing element disposed on an integrated circuit, the sensing element being removably attached to the enclosure, wherein the circuit comprises memory to store temperature data.

14. An apparatus comprising:
    an enclosure comprising a top cover and a bottom cover, at least one of the top cover or bottom cover comprising a surface that, in regular operation, is exposed to a gas; and
    a sensing element disposed on an integrated circuit, the sensing element being removably attached to the enclosure, wherein the enclosure is sealed to prevent ingress of air and moisture into the enclosure.

* * * * *